United States Patent [19]

King et al.

[11] Patent Number: 5,208,746
[45] Date of Patent: May 4, 1993

[54] METHOD FOR HELICAL SCANNING WITH A STATIONARY DETECTOR USING REBINNING AND SPLICING TO CREATE DETECTOR VERTEX PROJECTION SETS

[75] Inventors: Kevin F. King, New Berlin; Carl R. Crawford, Milwaukee, both of Wis.

[73] Assignee: General Electric Company, Milwaukee, Wis.

[21] Appl. No.: 440,566

[22] Filed: Nov. 22, 1989

[51] Int. Cl.⁵ .............................................. G06F 15/00
[52] U.S. Cl. ............................. 364/413.16; 364/413.15
[58] Field of Search ........................ 364/413.16, 413.17, 364/413.18, 413.19, 413.15; 378/4, 20, 14

[56] References Cited
U.S. PATENT DOCUMENTS 4,284,896  8/1981  Stonestrom .
4,630,202 12/1986  Mori .
4,789,929 12/1988  Nishimura et al. .
5,073,911 12/1991  Ozaki et al. ................... 364/413.15

Primary Examiner—Roy N. Envall, Jr.
Assistant Examiner—Xuong Chung
Attorney, Agent, or Firm—Quarles & Brady

[57] ABSTRACT

A method of reducing image helical scanning artifacts in fourth generation computed tomography imaging systems, rebins 360° of projection data into two half scans. The data of the half scans is spliced so as to create 360° of contiguous detector vertex projections. A weighting function is applied to the two half scans and they are reconstructed to an image per conventional reconstruction methods. The weighting functions provide effective interpolation and extrapolation of the half scan data to a slice plane centered in the projection data. In one embodiment, the weighting functions are feathered with a cubic function to remove weighting induced image artifacts.

5 Claims, 4 Drawing Sheets

METHOD FOR HELICAL SCANNING WITH A STATIONARY DETECTOR USING REBINNING AND SPLICING TO CREATE DETECTOR VERTEX PROJECTION SETS

BACKGROUND OF THE INVENTION

This invention relates to fourth generation computed tomography using helical scanning. More specifically, the invention concerns an image reconstruction method for reducing image artifacts that result from acquiring tomographic projection data in a helical scan.

In a fourth generation computed tomography system, an x-ray source is collimated to form a fan beam with a defined fan beam angle. The fan beam is orientated to lie within the x-y plane of a Cartesian coordinate system, termed the "imaging plane", and to be transmitted through an imaged object to an x-ray detector array orientated within the imaging plane. The x-ray source may be rotated on a gantry within the imaging plane, around the imaged object, so that the fan beam intercepts the imaged object at different angles.

The detector array is comprised of detector elements which each measure the intensity of transmitted radiation along rays projected from the x-ray source to that particular detector element. However, unlike the case of conventional third generation CT scanning where the detector array moves with the source, with a fourth generation system the detector array is fixed and so each detector element receives rays at a variety of angles as the source is rotated around the imaged object.

At each angle of the source, a data is acquired from each exposed detector element. This data, collected at a single source position, will be termed a "source-vertex" projection, and is similar to the projections acquired in third generation CT imaging.

The source is then rotated to a new angle and the process is repeated with the detectors receiving rays at new angles. The data for a given detector over 360° of source rotation will be termed a "detector-vertex" projection to be distinguished from the source-vertex projections described above. The detector-vertex projections are derived from the acquired source-vertex data.

The acquired detector-vertex projection set is typically stored in numerical form for computer processing to "reconstruct" a slice image according to detector-vertex reconstruction algorithms known in the art. The reconstructed slice images may be displayed on a conventional CRT tube or may be converted to a film record by means of a computer controlled camera. The use of detector-vertex projections in the reconstruction process rather than source-vertex projections reduces certain image artifacts associated with varying sensitivities among the detectors.

A typical computed tomographic study entails the imaging of a series of slices of an imaged object with the slices displaced incrementally along a z-axis perpendicular to the x and y axes, so as to provide a third spatial dimension of information. A radiologist may visualize this third dimension by viewing the slice images in order of position along the z-axis, or the numerical data comprising the set of reconstructed slices may be compiled by computer programs to produce shaded, perspective representations of the imaged object in three dimensions.

As the resolving power of computed tomography methods increases, additional slices are required in the z-dimension. The time and expense of a tomographic study increases with the number of slices required. Also, longer scan times increase the discomfort to the patient who must remain nearly motionless to preserve the fidelity of the tomographic reconstructions. Accordingly, there is considerable interest in reducing the time required to obtain a slice series.

The time required to collect the data for a series of slices depends in part on four components: a) the time required to accelerate the gantry to scanning speed, b) the time required to obtain a complete tomographic projection set, c) the time required to decelerate the gantry and d) the time required to reposition the patient in the z-axis for the next slice. Reducing the time required to obtain a full slice series may be accomplished by reducing the time required to complete any of these four steps.

The time required for acceleration and deceleration of the gantry may be avoided in tomographic systems that use slip rings rather than cables to communicate with the gantry. The slip rings permit continuous rotation of the gantry. Hereafter, it will be assumed that the CT systems discussed are equipped with slip rings or the equivalent to permit continuous rotation of over 360°.

The time required to acquire the tomographic data set is more difficult to reduce. Present CT scanners require on the order of one to two seconds to acquire the projection set for one slice. This scan time may be reduced by rotating the gantry at a faster speed. A higher gantry speed, in general, will reduce the signal-to-noise ratio of the acquired data by the square root of the factor of rotational rate increase. This may be overcome to some extent in transmission tomography devices by increasing the radiation output of the x-ray tube, but is subject to the power limits of such devices.

A reduction in patient repositioning time may be accomplished by translating the patient in the z-axis synchronously with the rotation of the gantry. The combination of constant patient translation along the z-axis during the rotation of the gantry and acquisition of projection data has been termed "helical scanning" and refers to the apparent path of a point on the gantry with respect to a reference point on the imaged body. As used herein, "helical scanning" shall refer generally to the use of continuous translation of the patient or imaged object during the acquisition of tomographic imaging data, and "constant z-axis scanning" shall refer to the acquisition of the tomographic data set without translation of the patient or imaged object during the acquisition period.

Continuous translation of the imaged object during scanning shortens the total scanning time required for the acquisition of a given number of slices by eliminating the length of time normally required for repositioning the patient between scans. However, helical scanning introduces certain errors with regard to the data in the acquired tomographic projection sets. The mathematics of tomographic reconstruction assumes that the tomographic projection set is acquired along a constant z-axis slice plane. The helical scan path clearly deviates from this condition and this deviation results in image artifacts in the reconstructed slice image if there is any significant change in the object in the z-axis. The severity of the image artifacts depends generally on the "helix offset" in the projection data, measured as the difference between the table locations of the scanned data and the z axis value of the desired slice plane. Errors resulting from helical scanning will be referred to collectively as "skew" errors.

Several methods have been used to reduce skew errors in helical scanning. A first approach disclosed in U.S. Pat. No. 4,789,929 issued Dec. 6, 1988, interpolates between projections of consecutive 360° tomographic projection sets. This approach of interpolating over 720° generally increases partial volume artifacts. Partial volume artifacts are image artifacts arising when certain volume elements of the imaged object contribute to only some of the projections of the projection set. In a second approach, described in co-pending U.S. patent application Ser. No. 07/435,980, filed Nov. 13, 1989 entitled "Extrapolative Reconstruction Method for Helical Scanning", and assigned to the same assignee as the present invention, skew artifacts are reduced by interpolating and extrapolating between two partial projection sets of only 180° of gantry rotation. This application is incorporated by reference.

SUMMARY OF THE INVENTION

It is understood in the art, that a tomographic image may be prepared from projection data acquired over less than 360° of gantry rotation. Generally, this result arises from the equivalence in attenuation of certain rays in projections acquired at gantry angles 180° apart. This method of reconstructing a tomographic image is termed "half scan" reconstruction. The weighting and reconstruction of images from a half scan data set are discussed in detail in "Optimal Short Scan Convolution Reconstruction for Fanbeam CT", Dennis L. Parker, Medical Physics 9(2) March/April 1982.

The present invention reduces skew artifacts in helically acquired data by interpolating and extrapolating a projection set with reduced helical offset from two detector-vertex half scans acquired near the slice plane. The half scans are created from data acquired over only $2\pi$ of gantry rotation by means of a splicing procedure.

Specifically, source-vertex projection data is acquired during $2\pi$ of gantry rotation and rebinned into corresponding detector-vertex projection sets. Two half scans are divided out of the rebinned detector-vertex projections set. The data from these half scans is spliced so as to create a full $2\pi$ of detector-vertex projections. The half scans are weighted to permit interpolation and extrapolation to the slice plane and then reconstructed to form an image.

It is one object of the invention to permit the acquisition of projection data for a single slice image over a shorter z-axis distance. The splicing process allows the detector-vertex half scans to be acquired in 360°. For a given scan pitch, the use of two detector-vertex half scans acquired in 360° rather than two full scans acquired in 720°, requires less z-axis travel in a helical scan. This in turn concentrates the projections acquired at points closer to the slice plane and thus improves the accuracy of the interpolation and extrapolation and decreases partial volume artifacts.

It is another object of the invention to permit the acquisition of projection data for a single slice image over a shorter time period. Image artifacts may result from patient motion during the acquisition of the projection data of a tomographic projection set. For a given gantry speed, the use of detector-vertex half scans acquired in only 360° of gantry rotation permits the reconstruction of images that are less susceptible to motion artifacts.

It is another object of the invention to improve the efficiency of the half scanning process. By splicing data acquired in 360° of gantry rotation to form the two detector-vertex half scans, the total x-ray exposure to the patient may be reduced.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

DETAILED DESCRIPTION OF THE PREFERRED EMBODIMENT

Figure 1:
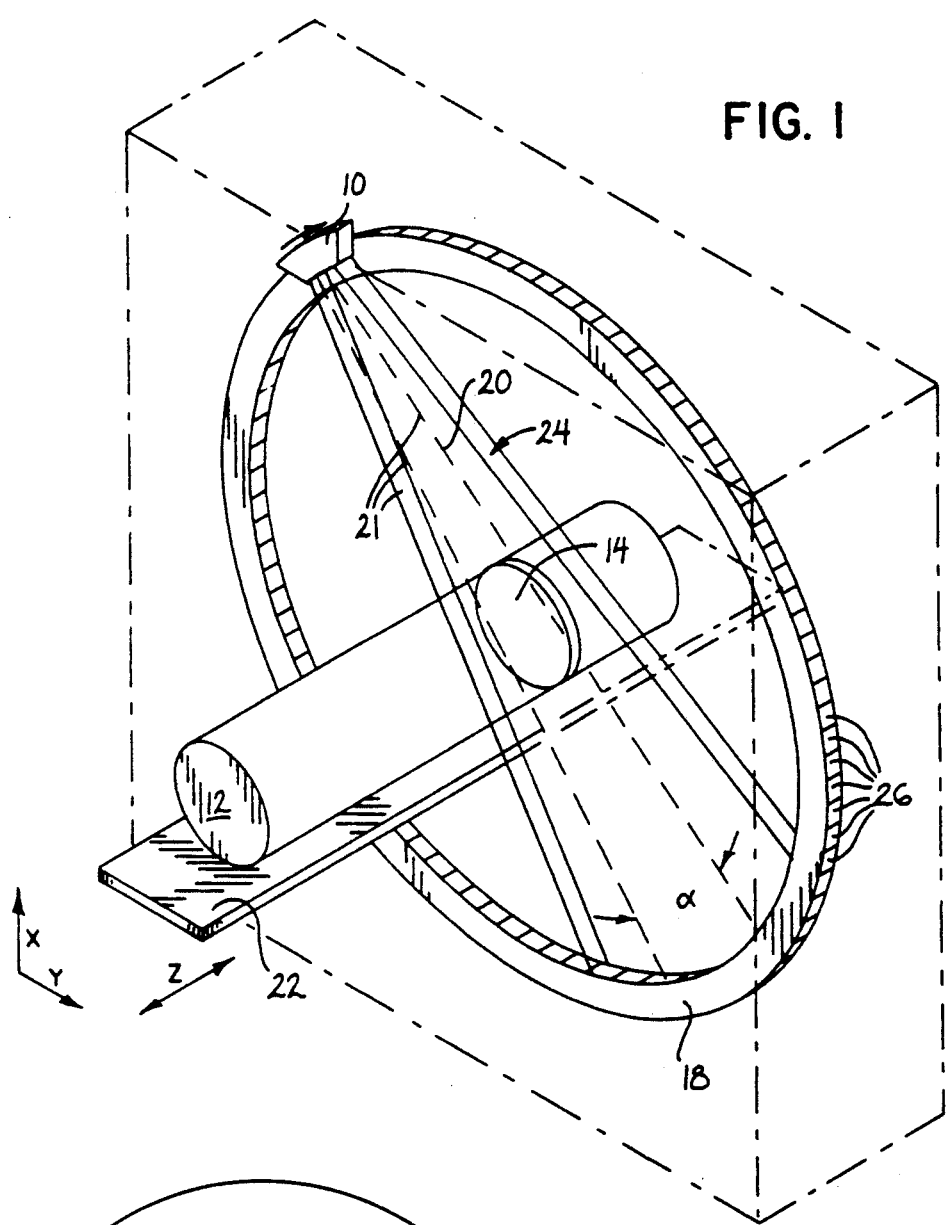
FIG. 1 is a pictorial representation of a fourth generation CT apparatus including gantry, table and imaged object, and showing the relative positions of the imaged object, the fixed detector array and the moving x-ray source.
Figure 2:
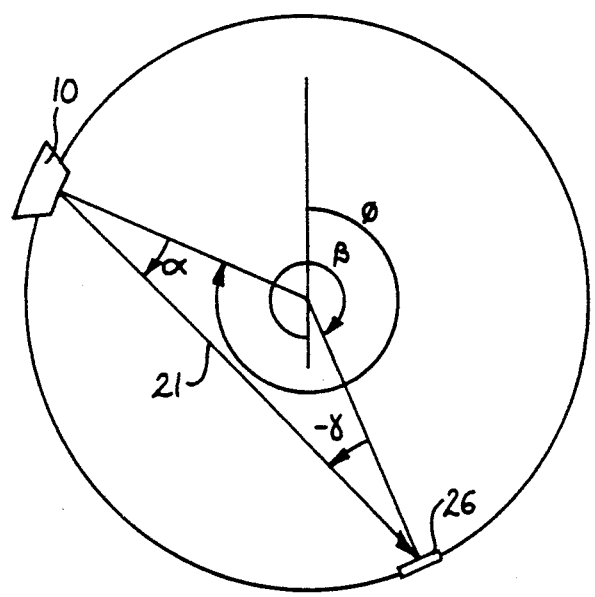
FIG. 2 is a diagram showing the geometry of a detector element with respect to the moving source and the variables describing their relative positions.

Referring to FIGS. 1 and 2, a CT gantry 16, a "fourth generation" CT scanner 16 includes an x-ray source 10 oriented to project a fan beam of x-rays 24 through imaged object 12 to stationary detector array 18. The fan beam 24 is directed along an x-y plane of a Cartesian coordinate system, the "imaging plane", and includes a plurality of rays 21 at angles $\alpha$ measured along the imaging plane from the centermost ray 20. The source 10 is attached to a gantry (not shown) to orbit the imaged object 12 at angle $\phi$ arbitrarily referenced to zero when the fan beam's center most ray 20 is vertical and directed downward. The source 10 is coupled to the gantry associated control modules 48, shown in FIG. 4 and to be described below, by means of slip rings (not shown) and is therefore free to rotate continuously through angles greater than 360° to acquire projection data.

The detector array 18 is formed in a ring lying substantially within the imaging plane and comprised of a number of detector elements 26 which together receive and detect a value proportional to the magnitude of a projected image resulting from the transmission of x-rays through the imaged object 12. The angle of the ray received by the detector element 26, for a given source 10 position $\phi$, is measured by $\gamma$ and referenced to a line of radius from the detector element 26 to the center of the ring of the detector array 18. The detector ring 18 may nutate to avoid interference with the rotating source 10.

As depicted in FIGS. 1 and 2, the radius of rotation of the source 10 and the radius of the ring of the detector array 18 are equal and hence $\alpha$ equals $-\gamma$. This choice of radii simplifies the following discussion, however, it will be understood to those of ordinary skill in the art that the radius of the detector ring may be made larger or smaller than the radius of the source's rotation with appropriate changes in the below described relationships between the detector and source-vertex projection sets.

The imaged object 12 rests on table 22 which is radio-translucent so as to minimize interference with the imaging process. Table 22 may be controlled so that its upper surface translates along the z axis perpendicular to the x-y imaging plane moving the slice plane 14 defined with respect to the imaged object 12 across the imaging plane swept by the fan beam 24. For simplicity, it will be assumed henceforth that the table 22 moves at a constant velocity and therefore that the z axis position of the table 22 is proportional to the angular position $\phi$ of the source 10.

Figure 3A:
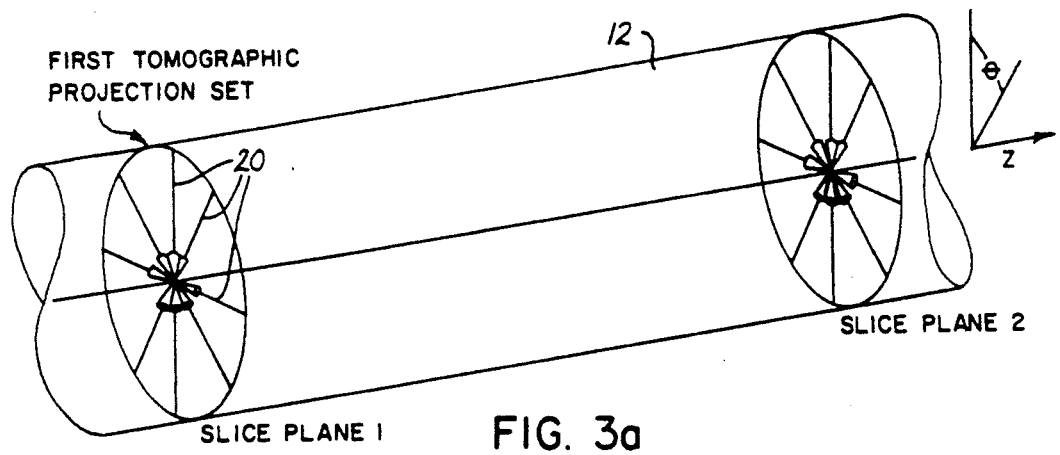
FIG. 3(a) and 3(b) are schematic illustrations of the imaged object of FIG. 1 showing the relative orientation of the gantry and imaging plane with respect to the imaged object for constant z axis scanning and helical scanning respectively. The pitch of the helical scanning is exaggerated for clarity.
Figure 3B:
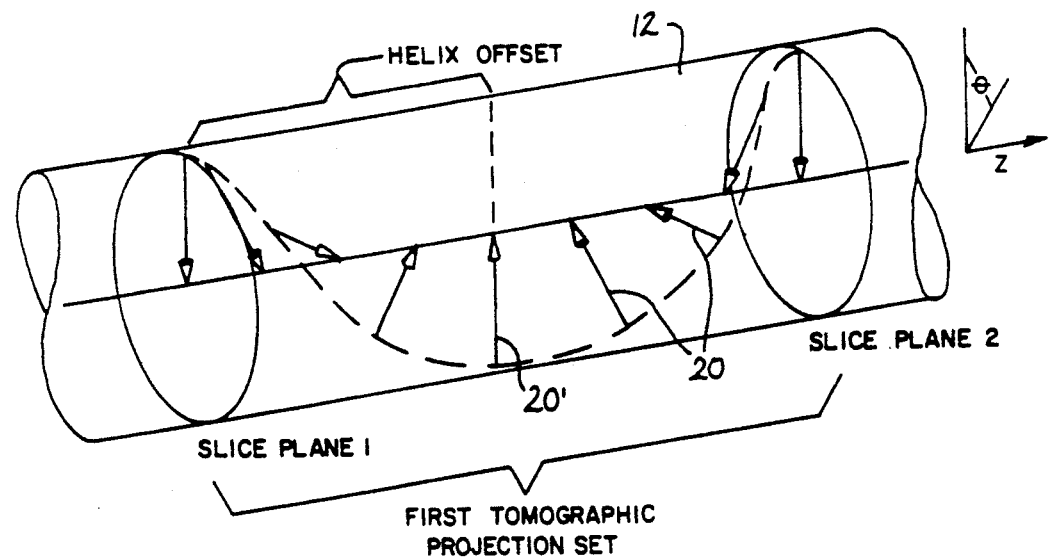

Referring to FIGS. 3(a) and 3(b), the angular position of the source 10 and the z-axis position of the imaging plane with respect to the imaged object is shown by projection arrows (equivalent to centermost ray 20) for a constant z-axis scan and a helical scan, respectively. In the constant z-axis scan, shown in FIG. 3(a) data is acquired at a constant z-axis position and the imaged object 12 is moved along the z-axis to the next slice plane 14 between such acquisitions.

This differs from the helical scan in FIG. 3(b) where the z-axis position of the imaged object 12 with respect to the imaging plane changes constantly during the acquisition of data. Accordingly, arrows 20 trace a helix within the imaged object 12 along the z-axis. The pitch of the helix will be referred to as the scanning pitch.

Figure 4:
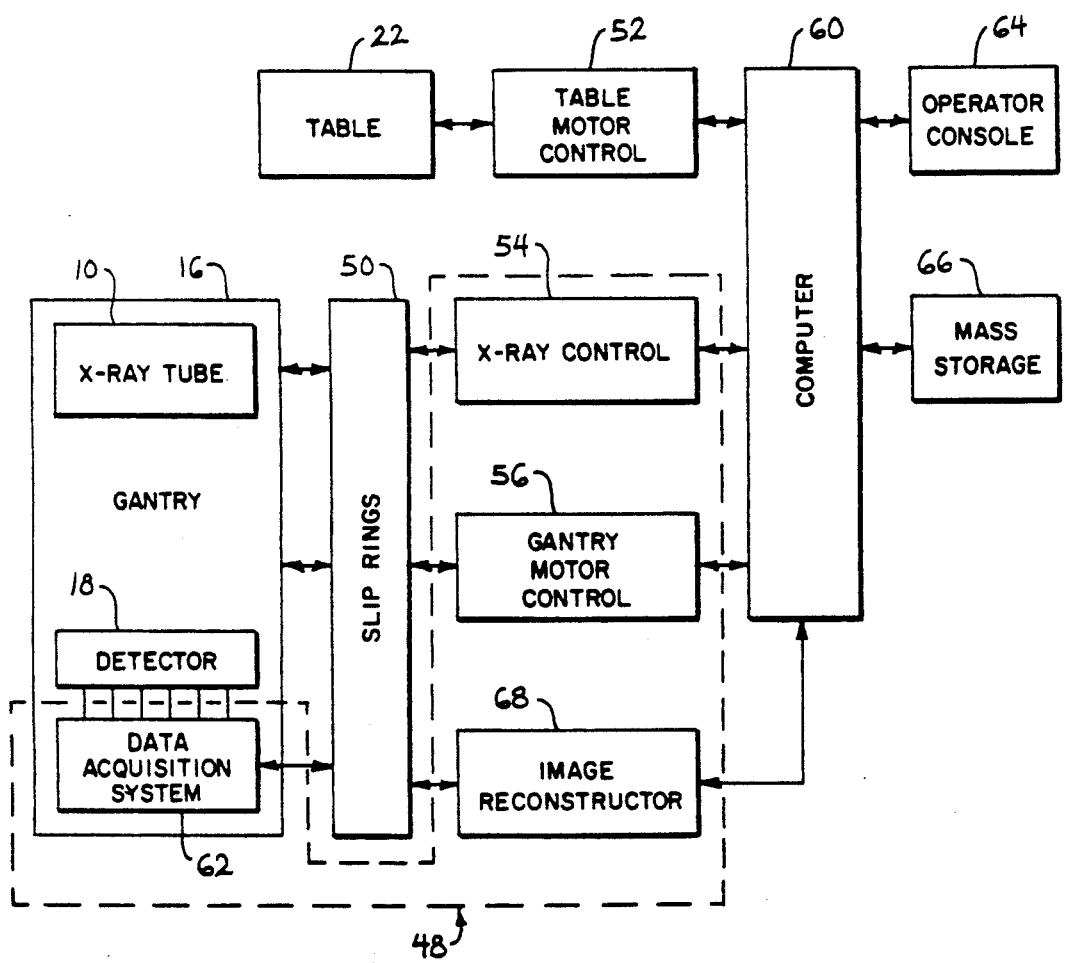
FIG. 4 is a block diagram of a CT control system that may be used with the CT apparatus of FIG. 1, and that is useful for practicing the present invention.

Referring now to FIG. 4, the control system of a CT imaging system suitable for use with the present invention has an x-ray control 54 which provides power and timing signals to the x-ray source 10, gantry motor controller 56 which controls the rotational speed and position of the source 10 and provides information to computer 60, and data acquisition system 62, regarding source 10 position, and image reconstructor 68 which receives sample and digitized signals from the detector array 18 via the data acquisition system 62 to perform high speed image reconstruction according to methods known in the art.

The speed and position of table 22 along the z-axis, is communicated to and controlled by computer 60 by means of table motor controller 52. The computer 60 receives commands and scanning parameters via operator console 64 which is generally a CRT display and keyboard which allows the operator to enter parameters for the scan and to display the reconstructed image and other information from the computer 60. A mass storage device 66 provides a means for storing operating programs for the CT imaging system, as well as image data for future reference by the operator.

Figure 5A:
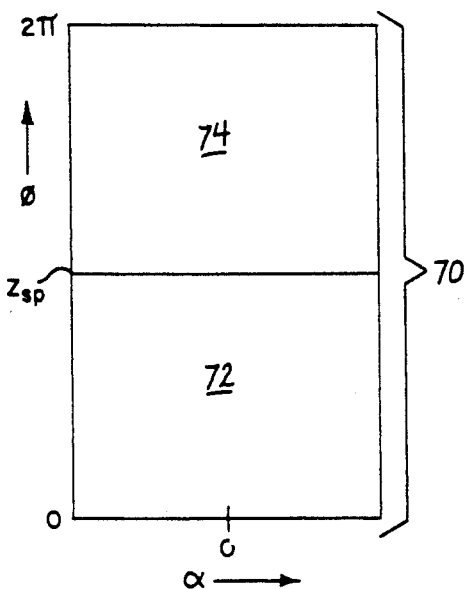
FIG. 5(a) is a graphical representation of the arguments $\phi$ and $\alpha$ associated with the projection data of two source-vertex partial projection sets acquired in a helical scan with the CT apparatus of FIG. 1.

Referring to FIG. 5(a) a source-vertex projection set 70 is acquired in two stages: first, the source angle $\phi$ is advance by $\pi$ to acquire a first partial fan beam projection set 72. The angle $\phi$ of the first projection will arbitrarily be designated $\phi=0$ regardless of the initial gantry angle. Hence the final projection will be at $\phi=\pi$. At the conclusion of this acquisition, the slice plane 14 of the imaged object 12 (shown in FIG. 1) has been aligned with the imaging plane corresponding to a z axis position of $z=z_{sp}$. A second partial fan beam projection set 74 is then initiated starting at gantry angle $\phi=\pi$ and continuing to gantry angle $\phi=2\pi$. As a result of the continuous table motion, the z axis position of the imaged object 12 is generally proportional to the gantry position $\phi$, that is:

$$z = k\phi \tag{1}$$

where k is a constant.

Figure 5B:
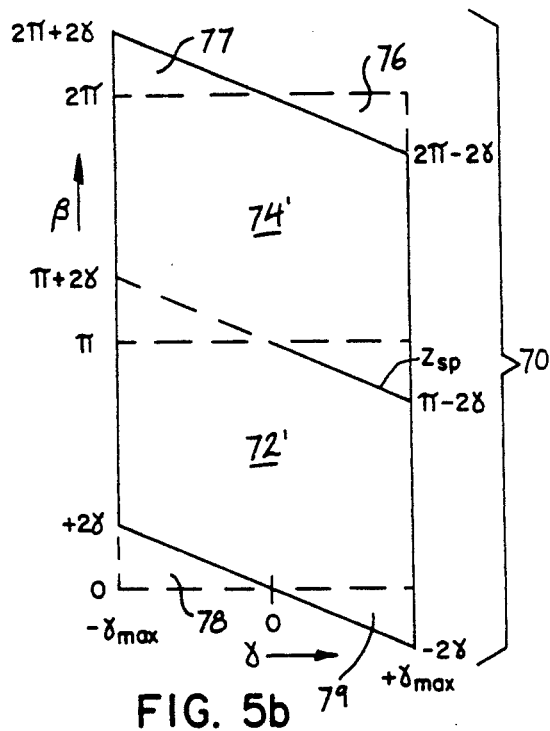
FIG. 5(b) is a graphical representation of the source-vertex partial projection sets of FIG. 5(a) rebinned to detector-vertex partial projection sets.

As the data 71 is acquired, it is sorted or "rebinned" as shown in FIG. 5(b), according to the following relationship:

For data element $P_{sv}(\phi, \alpha)$ in a source-vertex projection and $P_{dv}(\beta, \gamma)$ in the detector-vertex projection:

$$P_{sv}(\phi, \alpha) = P_{dv}(\phi + 2\alpha, -\alpha) \tag{2}$$

Regions 74 and 72 of FIG. 5(a) map to regions 74' and 72' of FIG. 5(b), respectively.

In non-helical third generation scanning an image may be formed from a "half scan" projection set containing less than $2\pi$ of projections by making use of the fact that rays traveling through the imaged object 12 along the same path but in opposite directions provide similar data. In an analogous manner, images may be reconstructed from a detector-vertex half scan projection. Specifically, for any two points in a detector-vertex projection set, $P_1$ and $P_2$, acquired in a non-helical scan:

$$P_1(\beta, \gamma) = P_2(\beta + \pi + 2\gamma, -\gamma) \tag{3}$$

This relationship does not hold exactly in helical scanning. The imaged object 12 moves with rotation of the gantry 16 and hence the projection data obtained for two rays 21 of opposing angle will differ. Nevertheless, the relation (3) above describes pairs of data elements between projections that may be expected to be more highly correlated than other pairs of data elements. The relationship of equation (3) for data obtained from helical scanning will be termed "redundancy".

Figure 6A:
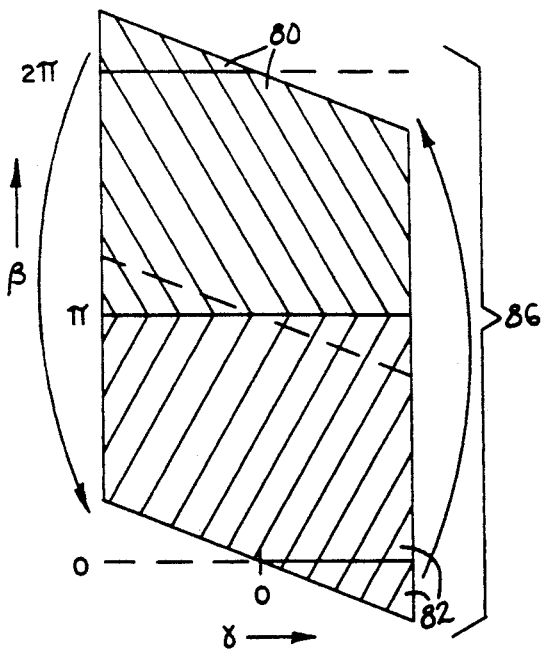
FIG. 6(a) is a graphical representation of a first and second half scan divided from the rebinned projections of FIG. 5(b)

Referring to FIG. 6(a), the detector-vertex projection sets of FIG. 5(b) may be divided into two equal regions 80 and 82 of corresponding redundant data per equation (3) above. Each of these regions could be used to reconstruct the full detector-vertex projection set 71 and hence each region 80 and 82 is also a half scan.

The reconstruction methods for fourth generation detector-vertex projection sets require a complete detector-vertex projection set. A complete, detector-vertex projection set comprises projections over $2\pi$ of detector elements 26 each containing rays acquired over $2\gamma_{max}$ where $\gamma_{max}$ is determined by the maximum angle subtended by the imaged object 12. Referring to FIG. 5(a) and 5(b), the rebinning of $0<\phi<2\pi$ of source-vertex projections does not completely fill $0<$-

$\beta < 2\pi$ of detector vertex projections. Specifically, only partial projections are available for the region $2\pi > \beta > 2\pi - 2\gamma$ identified as region 76 and for the region $0 < \beta < 2\gamma$ identified as region 78.

Figure 6B:
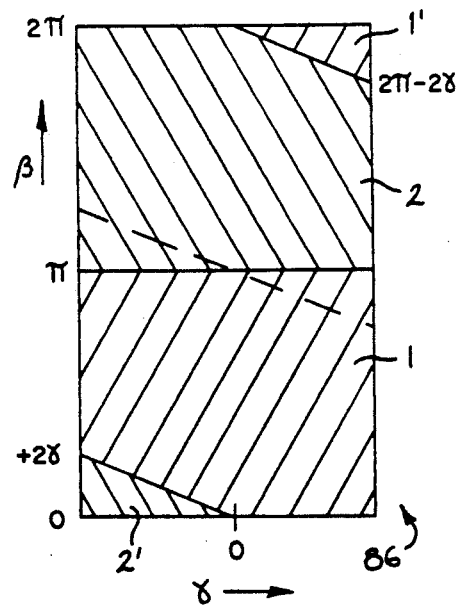
FIG. 6(b) is a graphical representation of a 360° detector-vertex projection set spliced from the first and second detector-vertex half scans.

Accordingly, in order to obtain $2\pi$ of detector-vertex projections for reconstruction into an image, data is "spliced into areas 76 and 78 from elsewhere in the detector-vertex data. Such spliced data is preferably related to the missing data of regions 76 and 78 by the redundancy equation (3) above. Also, it is preferable for reasons of signal-to-noise ratio to splice data from areas that would otherwise be unused in the reconstruction process. Regions 77 where $2\pi < \beta < 2\pi + 2\gamma$ and 79 where $-2\gamma < \beta < 0$ satisfy these requirements. Accordingly, the data of region 79 is spliced into region 76 and the data of region 77 is spliced into region 78 according to the relationship of equation (3) and as shown in FIG. 6(b).

It will be apparent from the above description that other regions may be spliced to similar effect. For example, the entire region 82 may be spliced to the top of region 80 by shifting the data of region 82 by $2\pi$. Again, the net effect is to create $2\pi$ of complete detector vertex projections.

The data of the two half scans 80 and 82, as spliced to form data set 86, may now be interpolated and extrapolated to the slice plane by weighting their data according to its displacement from the slice plane and reconstructing both 80 and 82 as a single $2\pi$ of detector-vertex projection set. The summing of the weighted data required for the interpolation and extrapolation is carried out by the image reconstruction process as is understood in the art.

The interpolation and extrapolation weights required for each data element in the spliced detector-vertex projection set will depend on the data element's distance from the slice plane relative to the distance from the slice plane of its corresponding redundant data element per equation (3) above. The weighting is accomplished by multiplying the values of the redundant data elements by their respective weights.

Specifically, for any two redundant data elements $P_1(\beta_1, \gamma_1)$ it appears at Z, and $P_2(\beta_2, \gamma_2)$ at $z_2$, the weight $w_1$ for point $P_1$ for linear interpolation or extrapolation to a slice plane at $z_{sp}$ is:

$$w_2 = \frac{z_{sp} - z_1}{z_2 - z_1} \quad (4)$$

and for data element $P_2$ the weight $w_2$ is:

$$w_1 = 1 - w_2 \quad (5)$$

Calculation of these weights requires that the redundant data elements within the spliced detector-vertex projection set 86 of FIG. 6(b) be determined. Referring to FIG. 6(a), regions 80 and 82 are redundant per equation (3) and therefore require separate weighting functions per equation (4) and (5) above. Further, the splicing operation displaced some of the data elements of regions 8 and 82 creating regions of dislocated data that require additional unique weighting functions that account for the dislocation.

Referring to FIG. 6(b), the result of the splicing operation is to create four regions within the spliced data set 86, of $0 < \beta < 2\pi$, each which will require a different weight.

| Region | Argument |
|---|---|
| 1 | $\beta^3 >$ |
| 2 | $\pi < \beta < 2\pi - 2\gamma$ |
| 1' | $\beta > 2\pi - 2\gamma$ |
| 2' | $\beta < -2\gamma$ |

Regions 1' and 2' are named to reflect their origins as portions of set 82 and 80, now identified as region 1 and 2 in FIG. 6(b). The data in Regions 1 and 1' are redundant with data in Regions 2 and 2'.

With the regions of corresponding redundant data elements identified, the z values of the data elements of those regions must be determined. The z value of each data element is proportional to the value of $\phi$ for the corresponding data element of the fan beam projection set per equation (1) above. Therefore:

$$z(\beta, \gamma) = k\phi \quad (6)$$
$$= k(\beta + 2\gamma) \text{per equation (2)} \quad (7)$$

The z value of the slice plane is $k(\pi)$ as defined previously.

The weighting function $w_1(\beta, \gamma)$ for region 1 may be now readily determined.

$$w_1 = \frac{\beta}{\pi - 2\gamma} \quad (8)$$

Similarly, for region 2 the weighting factor is:

$$w_2 = \frac{2\pi - \beta}{\pi + 2\gamma} \quad (9)$$

The weighting factor for region 1' is the same as that for region 1 but shifted by $2\pi$ as a result of the splicing procedure. Hence:

$$w_{1'} = \frac{\beta - 2\pi}{\pi - 2\gamma} \quad (10)$$

And for region 2', $w_{2'}$ is:

$$w_{2'} = \frac{-\beta}{\pi + 2\gamma} \quad (11)$$

The boundary between the regions 1 and 2' and the boundary between regions 1' and 2 will have discontinuities as a result of the discontinuities in the weighting factors used for the interpolation of the data described above. These discontinuities may create streak image artifacts in the final image. The discontinuity may be eliminated by feathering $w_1$, $w_1'$, $w_2'$ and $w_2'$ near the interfaces of their regions. The feathering is performed over an area between the regions of height $\omega$. A value of $\omega$ equivalent to the angle subtended by ten source 10 increments is believed to be sufficient.

Specifically, $w_1$, $w_1'$, $w_2$, and $w_2'$ are multiplied by respective feathering functions $f_1(\beta, \gamma)$, $f_1'(\beta, \gamma)$, $f_2(\beta, \gamma)$, $f_2'(\beta, \gamma)$ and the product applied to the data of the entire projection set where:

$$f_1(\beta, \gamma) = \begin{cases} 3x^2(\beta) - 2x^3(\beta) & \text{for } -2\gamma - \omega/2 \leq \\ & \beta \leq -2\gamma + \omega/2 \\ 1 & \text{for } \pi > \beta > -2\gamma + \omega/2 \\ 0 & \text{elsewhere} \end{cases} \quad (12)$$

for $$x(\beta, \gamma) = \frac{\gamma + \frac{\beta}{2}}{\omega} + .5 \quad (13)$$

and $$f_2(\beta, \gamma) = \begin{cases} 3x^2(\beta) - 2x^3(\beta) & \text{for } 2\pi - 2\gamma - \omega/2 \leq \\ & \beta \leq 2\pi - 2\gamma + \omega/2 \\ 1 & \text{for } \pi > \beta > \\ & 2\pi - 2\gamma - \omega/2 \\ 0 & \text{elsewhere} \end{cases} \quad (14)$$

where $$x(\beta, \gamma) = \frac{-\gamma + \pi - \frac{\beta}{2}}{\omega} + .5 \quad (15)$$

and $$f_{1'}(\beta, \gamma) = \begin{cases} 3x^2(\beta) - 2x^3(\beta) & \text{for } 2\pi - 2\gamma - \omega/2 \leq \\ & \beta \leq 2\pi - 2\gamma + \omega/2 \\ 1 & \text{for } \beta > 2\pi - 2\gamma + \omega/2 \\ 0 & \text{elsewhere} \end{cases} \quad (16)$$

where $$x(\beta, \gamma) = \frac{\gamma - \pi + \frac{\beta}{2}}{\omega} + .5 \quad (17)$$

$$f_{2'}(\beta, \gamma) = \begin{cases} 3x^2(\beta) - 2x^3(\beta) & \text{for } -2\gamma - \omega/2 \leq \\ & \beta \leq -2\gamma + \omega/2 \\ 1 & \text{for } \beta < -2\gamma - \omega/2 \\ 0 & \text{elsewhere} \end{cases} \quad (18)$$

where $$x(\beta, \gamma) = \frac{-\gamma - \frac{\beta}{2}}{\omega} + .5 \quad (19)$$

Many modifications and variations of the preferred embodiment which will still be within the spirit and scope of the invention will be apparent to those with ordinary skill in the art. For example, other interpolation or extrapolation methods may be used including those using data from additional half scans before and after the half scans on either side of the slice plane and those using higher order interpolation methods. Further this method may be utilized in situations where the gantry does not move at a constant speed with respect to the table, provided the z-axis position associated with each data element may be determined. Finally, for the purposes of simplifying the discussion, it has been assumed that the gantry is positioned at $\pi$ radians when the slice plane is crossed. Clearly, any starting gantry angle is acceptable, provided the partial projection sets are properly referenced from the gantry position at the slice plane. The extrapolation method describes also means that the slice plane need not be centered within the half scan data.

We claim:

1. A method producing a tomographic image of an imaged object from data acquired in a helical scan, the data acquired as a series of source-vertex projections at a plurality of gantry angles $\phi$ about a z-axis and within an image plane at detectors at detector angles $\beta$, the source-vertex projections including a plurality of data at ray angles $\alpha$, comprising the steps of:

(a) identifying a slice plane $z_{sp}$ relative to the imaged object and parallel to the image plane;

(b) acquiring a source-vertex projection set of data over $2\pi$ of source rotation;

(c) moving the imaged object along the z-axis and rotating the source so that the imaging plane crosses the slice plane during the acquisition of a source-vertex projection set;

(d) rebinning the source-vertex projection set into a detector vertex projection set including redundant data and missing data relative to a complete detector-vertex projection set;

(e) dividing the detector-vertex projection set into two half scans, each including portions of the redundant data and the missing data;

(f) splicing data between the half scans by using the redundant data of each half scan as the missing data from the other half scan to create a complete detector-vertex projection set over $2\pi$ of detector angle $\beta$, the splicing being effected by changing at least the gantry angle $\beta$ of the redundant data;

(g) extrapolating and interpolating the data of the half scans into a slice plane detector-vertex projection set; and (h) reconstructing the slice plane detector-vertex projection set into a slice image.

2. The method of claim 1 where the data of the half scan are extrapolated and interpolated per step (g) by applying a weighting function to the half scans and reconstructing the half scans as weighted and after splicing per step (f) into a slice image per step (h).

3. The method of claim 2 wherein the weighting function for pairs of redundant data within the each half scan add to a constant and the weight for any such datum is a function of $\phi$.

4. The method of claim 1 including the step of applying a feathering weighting to the half scans.

5. The method of claim 1 where the slice plane crosses the imaging plane midway through the acquisition of the source vertex projection set.

* * * * *